US006571003B1

(12) United States Patent
Hillebrand et al.

(10) Patent No.: US 6,571,003 B1
(45) Date of Patent: May 27, 2003

(54) SKIN IMAGING AND ANALYSIS SYSTEMS AND METHODS

(75) Inventors: Greg George Hillebrand, Wyoming, OH (US); Kukizo Miyamoto, Hyogo (JP); Brian Dale Barford, West Chester, OH (US); Joseph Michael Miller, Cincinnati, OH (US); Mark Steven Hayworth, Cincinnati, OH (US); Michael Lee Hilton, Fairfield, OH (US); Gary Gordon Heaton, Loveland, OH (US); Michael Eugene Rubush, West Chester, OH (US)

(73) Assignee: The Procter & Gamble Company, Cincinnati, OH (US)

( * ) Notice: Subject to any disclaimer, the term of this patent is extended or adjusted under 35 U.S.C. 154(b) by 0 days.

(21) Appl. No.: 09/333,136

(22) Filed: Jun. 14, 1999

(51) Int. Cl.⁷ .................................................. G06K 9/00
(52) U.S. Cl. ...................................... 382/118; 382/100
(58) Field of Search ................................. 382/100, 128, 382/118, 115; 128/922; 348/77, 78, 80; 600/306

(56) References Cited

U.S. PATENT DOCUMENTS

| | | | |
|---|---|---|---|
| 4,276,570 A | 6/1981 | Burson et al. | 358/903 |
| 4,871,262 A | 10/1989 | Krauss et al. | 366/160 |
| 4,894,547 A | 1/1990 | Leffell et al. | 250/461.2 |
| 5,016,173 A | 5/1991 | Kenet et al. | 364/413.13 |
| 5,622,692 A | 4/1997 | Rigg et al. | 424/63 |
| 5,781,650 A | 7/1998 | Lobo et al. | 382/118 |
| 5,785,960 A | 7/1998 | Rigg et al. | 424/63 |
| 5,796,862 A | 8/1998 | Pawlicki et al. | 382/132 |
| 5,836,872 A | 11/1998 | Kenet et al. | 600/306 |

FOREIGN PATENT DOCUMENTS

| | | | |
|---|---|---|---|
| DE | 196 22 569 A1 | 12/1997 | A61B/5/107 |
| GB | 2147421 B | 5/1985 | |
| JP | 2148495 B | 5/1985 | |
| JP | 5-253191 | 10/1993 | |
| JP | 6-309527 | 11/1994 | |
| JP | 7-100126 | 4/1995 | |
| JP | 5-247523 | 9/1995 | |
| JP | 7-231883 | 9/1995 | |
| JP | 8-280633 | 10/1996 | |
| JP | 10-65928 | 3/1998 | |
| WO | 97/47235 | 12/1997 | A61B/5/00 |
| WO | 98/37811 | 9/1998 | A61B/6/08 |

OTHER PUBLICATIONS

Patent Abstracts of Japan, Publication No. 05–253210, "Wrinkle Measuring System," May 10, 1993.

Primary Examiner—Samir Ahmed
Assistant Examiner—Vikkram Bali
(74) Attorney, Agent, or Firm—Jack L. Oney

(57) ABSTRACT

The apparatus and method of the present invention provides a process that can be implemented by a human operator and a computing device to analyze and display human skin images. The system acquires a digital image from a camera or scanner. Subsequently, the system determines which area(s) of the image to analyze using landmarks such as the corner of the eye. The determined areas are then analyzed to locate skin defects such as red spots, and the defects are visually identified on a display. A severity is calculated for the defects and the severity is compared to an average skin severity associated with a population of people. In addition, a simulation is generated and displayed showing an improvement to the defect areas.

41 Claims, 16 Drawing Sheets

SKIN IMAGING AND ANALYSIS SYSTEMS AND METHODS

TECHNICAL FIELD OF THE INVENTION

The present invention relates in general to an apparatus and methods for displaying information associated with a plurality of skin defects and in particular for determining and displaying the location of one or more analysis areas and defect areas associated with a digital image of human skin and for determining the severity of these defects as well as displaying an improvement and/or worsening to the defect areas.

BACKGROUND OF THE INVENTION

Countless individuals all over the world seek to improve their physical appearance through the use of cosmetics and skin care treatments. As a result there is an extremely large choice of available products for consumers to choose from. Often, the individual consumer finds it difficult to determine what type of products to apply and how to apply them to best improve their own personal skin type and condition. This problem is compounded as the individual's skin condition changes over time and/or society's norms change over time.

Beauty counselors at retail cosmetics counters are charged with identifying defects in a client's skin. Once the defects are identified the counselor must communicate the type, quantity, and location of those defects to the client for discussion. Finally, the counselor must recommend products and application techniques aimed at improving the appearance of the identified defects and demonstrate the improvement to the customer.

Typically, such consultations are very subjective. Not all beauty counselors identify the same type or number of skin defects. Consultation results can vary from visit to visit, even with the same counselor and client. Often, it is difficult for the counselor to communicate the defects she is seeing to the client, and the trial and error process of testing recommendations is time consuming and tedious.

SUMMARY OF THE INVENTION

The present invention is directed to a method and apparatus for analyzing a plurality of visual skin defects. The method and apparatus provide quick identification of the skin defects in a user friendly manner thereby allowing an operator to recommend cosmetic products or medical treatments and simulate an improvement and/or worsening to the areas.

In one aspect, the invention is directed to a system for locating a plurality of visual skin defects associated with the face of a person. The system acquires a first digital image of the face of the person and electronically analyzes the first digital image of the face of the person to locate a plurality of defect areas. Each defect area is typically much smaller than the first digital image, and each defect area contains at least one visual skin defect. Subsequently, the system electronically creates and displays a second digital image, based on the first digital image, of the face of the person and the location of the defect areas. The second digital image visually identifies the plurality of defect areas located in the first digital image by electronically altering the color of a plurality of pixels substantially in the area containing the skin defect (i.e., on or around the defect area) to at least one color visually distinct from the skin color of the first digital image.

In another aspect, the invention is directed to a system for locating a plurality of visual skin defects associated with the face of a person. The system acquires a first digital image of the face of the person and identifies a plurality of landmarks located in the first digital image of the face of the person such as a corner of an eye, a corner of a nose, and/or a corner of a mouth. Subsequently, the system electronically determines a sub-image of the first digital image of the face of the person based on the plurality of landmarks. This sub-image is then electronically analyzed to locate a plurality of defect areas. Each defect area is typically much smaller than the first digital image, and each defect area contains at least one visual skin defect.

In yet another aspect, the invention is directed to a system for simulating an improvement and/or worsening to a plurality of visual skin defects associated with the face of a person. The system acquires a first digital image of the face of the person and electronically analyzes the first digital image of the face of the person to locate a plurality of defect areas. Each defect area is typically much smaller than the first digital image, and each defect area contains at least one visual skin defect. Subsequently, the system electronically creates and displays a second digital image based on the first digital image of the face of the person and the location of the defect areas. The second digital image comprises an improved (or worsened) area for each of the plurality of defect areas. Each of the improved (or worsened) areas is created by electronically altering the color of a plurality of pixels in one of the plurality of defect areas located in the first digital image of the face of the person.

These and other features and advantages of the present invention will be apparent to those of ordinary skill in the art in view of the detailed description of the preferred embodiment which is made with reference to the drawings, a brief description of which is provided below.

DETAILED DESCRIPTION OF THE PREFERRED EMBODIMENTS

Figure 1:
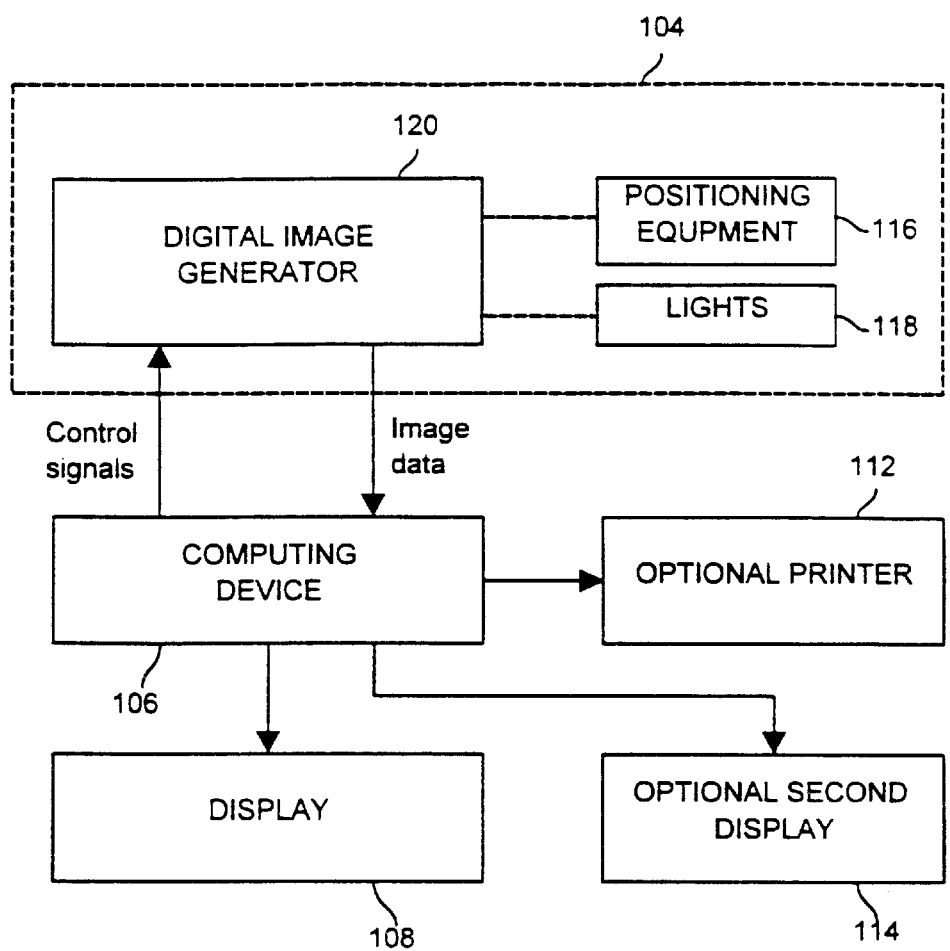
FIG. 1 is a block diagram of an imaging apparatus capable of utilizing the present invention.

A block diagram of an imaging apparatus capable of utilizing the present invention is illustrated in FIG. 1. In one embodiment, the imaging apparatus is located at a retail cosmetics counter for the purpose of analyzing and recommending cosmetic and skin care products. However, persons of ordinary skill in the art will readily appreciate that the apparatus may be used anywhere without departing from the scope and spirit of the present invention. For example, the apparatus could be used in a doctor's office for diagnostic purposes and archiving patient data. The apparatus may include an imaging rig 104 which is connected to a computing device 106 for the purpose of acquiring images of human skin to be analyzed. For simplicity and consistency, the imaging of a human face is described herein. However, persons of ordinary skill in the art will readily appreciate that other areas of the body (e.g., a hand, an arm, a leg, etc.) may be imaged.

The imaging rig 104 may include positioning equipment 116, lights 118, and a digital image generator 120 such as a digital camera, an analog camera connected to a digitizing circuit, a scanner, a video camera, etc. The devices in the imaging rig 104 may be arranged at predetermined distances and predetermined angles relative to one another to maximize the quality of the acquired image. For example, a positioning device for stabilizing the face of a person may include a chin rest and/or a forehead rest. In one embodiment, the digital image generator 120 is placed at a predetermined distance and a predetermined angle relative to the positioning device.

The computing device 106 is also connected to one or more output devices such as a first display 108, a second display 114, and/or a printer 112. Each display 108, 114 may be a cathode ray tube (CRT), liquid crystal display (LCD), or any other type of display. The printer may be a laser printer, ink jet printer, or any other type of printer. The displays 108, 114 generate images which may include operator prompts, preferences, options, and digital images of skin. The optional printer 112 may be used to print out digital images and/or analysis results for the analyzed person.

Figure 2:
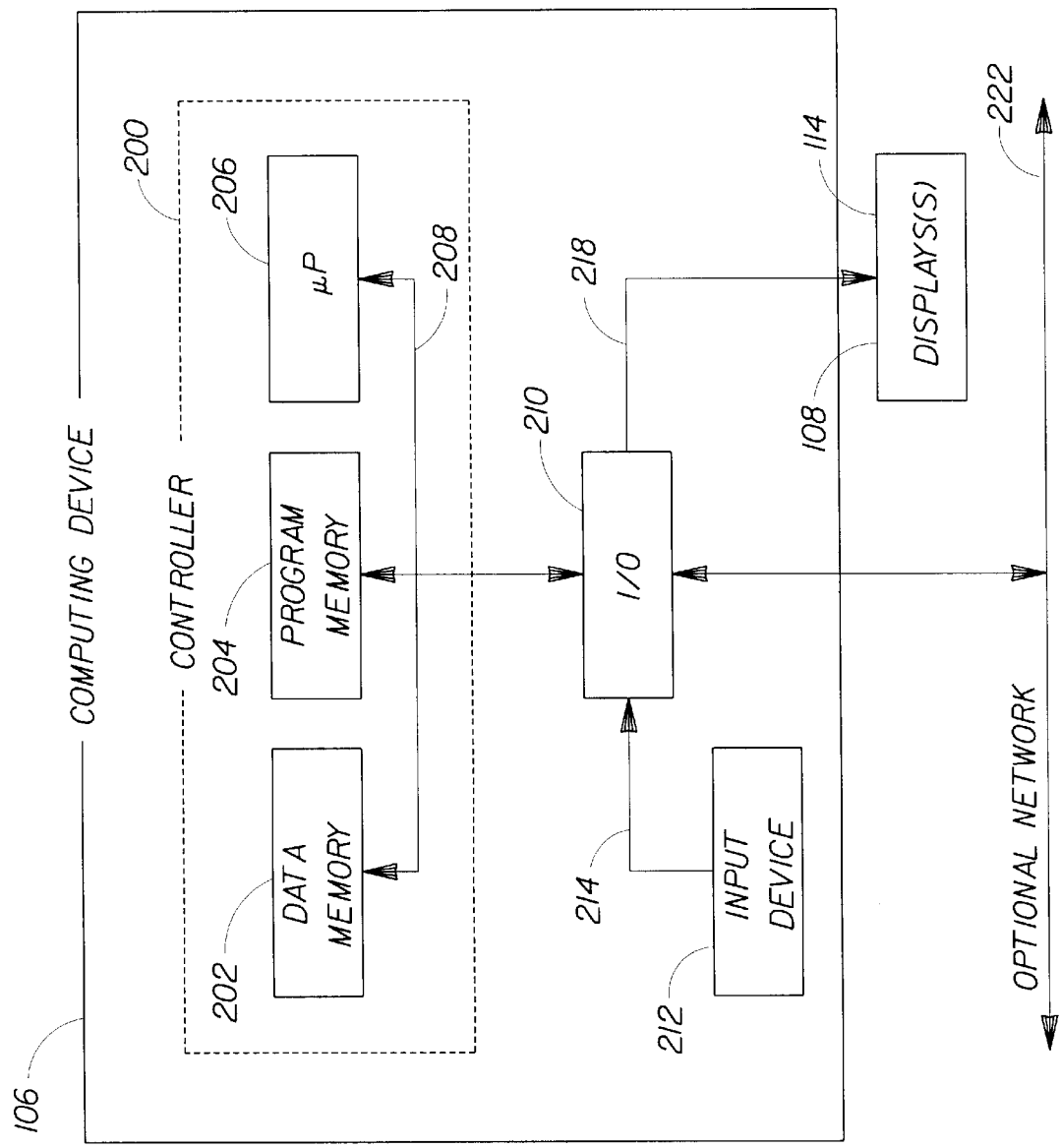
FIG. 2 is a more detailed block diagram of the computing device of FIG. 1.

A more detailed diagram of the computing device 106 is illustrated in FIG. 2. The computing device 106 may be a general purpose computer programmed to implement the method and/or apparatus of the present invention, or the computing device 106 may be an application specific device designed to implement the method and/or apparatus of the present invention as is well known to persons of ordinary skill in the art. A controller 200 in the computing device 106 may include a data memory 202, such as a random-access memory and/or a disk drive, a program memory 204, which may be in the form of a read-only memory (ROM), and a microprocessor 206, all of which may be interconnected by an address/data bus 208. In one embodiment, the program memory 204 electronically stores a computer program that implements all or part of the method described below, and the program is executed by the microprocessor 206. The program memory 204 may be loaded from a fixed memory device such as a hard drive, or the program memory 204 may be preloaded with firmware as is well known to persons of ordinary skill in the art. Some of the steps described in the method below may be performed manually or without the use of the computing device 106.

A transmitter and receiver in the form of a conventional input/output (I/O) circuit 210, such as a modem for example, typically couples the controller 200 to a communication channel such as an optional network 222 (e.g., a local area network, the Internet, etc.). The network 222 may be used to acquire digital images and/or other information used in the process described below. An input device 212 such as a keyboard and/or mouse may be connected to the I/O circuit 210 via a line 214 for entering data and commands into the controller 200. Further, the displays 108, 114 may be connected to the I/O circuit 210 to receive data via a line 218 to generate visual displays of data generated during operation of the computing device 106.

Overall Operation

Figure 3:
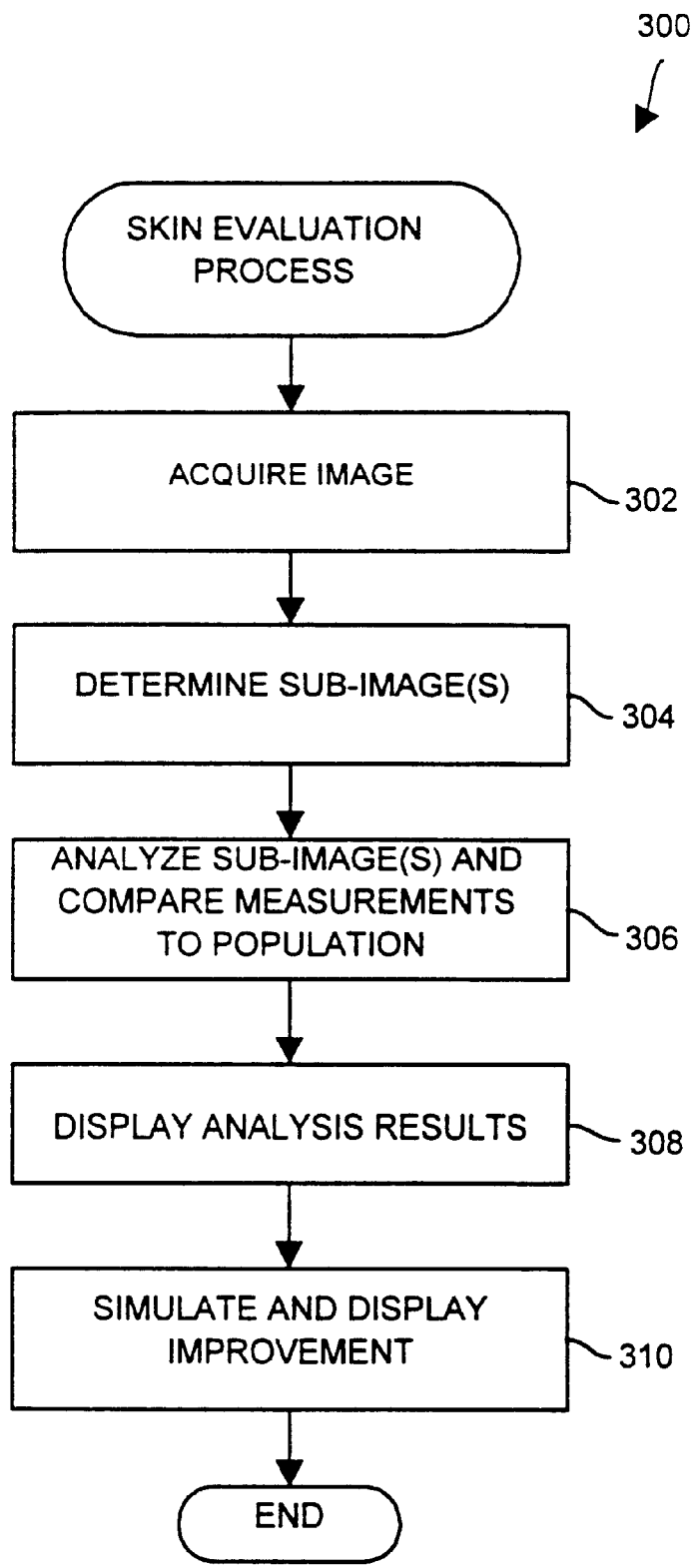
FIG. 3 is a flow chart of a process that can be implemented by a human operator and the computing device of FIG. 2 to analyze and display images in accordance with the teachings of the present invention.

A flow chart of a process 300 that can be implemented by a human operator and the computing device 106 to analyze and display images in accordance with the teachings of the present invention is illustrated in FIG. 3. In one embodiment, the programmed steps performed by the computing device 106 are executed by the controller 200. When the process 300 is initiated, the controller 200 acquires an image (step 302), determines which area(s) of the image to analyze (i.e., a sub-image) (step 304), analyzes those areas to locate defects (step 306), compares the severity of the located defects to an average skin severity or other statistical parameter associated with a population of people (step 306), displays the analysis results (step 308), and simulates an improvement and/or worsening to the defect areas (step 310). Each of these steps is described in detail below.

Image Acquisition

Figure 4:
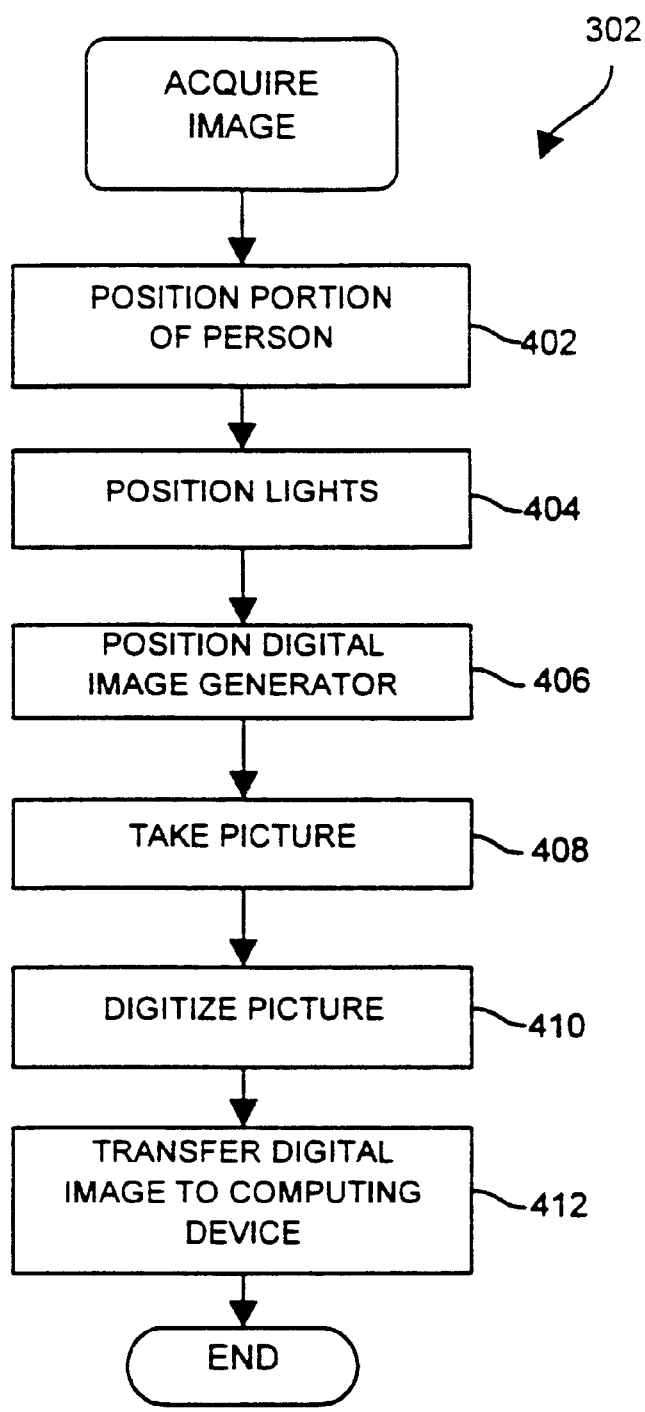
FIG. 4 is a detailed flow chart of a process of acquiring images in accordance with the teachings of the present invention.

A detailed flow chart of the process 302 (shown schematically in FIG. 3) of acquiring images in accordance with the teachings of the present invention is illustrated in FIG. 4. In one embodiment, the steps are performed by an human operator and the controller 200. The process 302 begins at step 402 when the operator positions a portion of the person to be analyzed (e.g., the face) in the imaging rig 104. For ideal image acquisition, sufficient and consistent lighting is desired. At steps 404 and 406, the lights 118 and the digital image generator 120 (e.g., a camera) may be positioned after the person's face is positioned in order to maximize image quality. Alternatively, the lights 118 and digital image generator 120 may be positioned in a desired location prior to positioning of the face to expedite the image acquisition process.

When the lights 118, digital image generator 120, and face are in position, a picture is taken at step 408 in response to a command from the operator. At step 410, the picture is digitized (i.e., converted to a binary representation) in a known manner. Finally, at step 412, the digital image data is transferred to the computing device 106. Many other methods of acquiring the digital image are well known to persons of ordinary skill in the art. For example, the person to be analyzed may submit a picture via the network 222, a file may be retrieved from a database, and/or a flatbed scanner may be used to digitize an analog photograph.

Graphical User Interface

Figure 5:
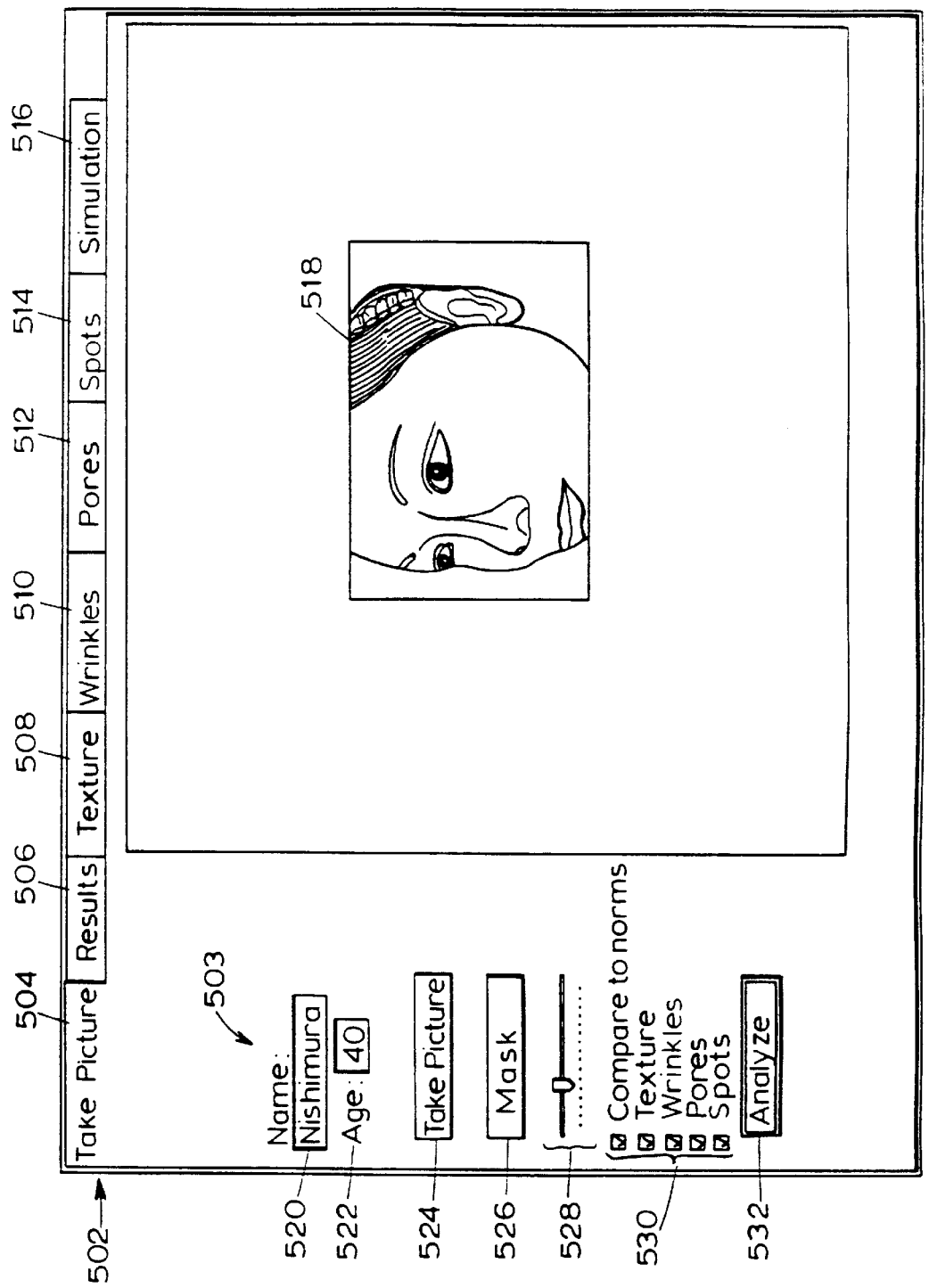
FIG. 5 is a line drawing of a graphical user interface that can be implemented by the computing device and display of FIG. 1 to display an acquired image in accordance with the teachings of the present invention.

A line drawing of a graphical user interface that can be implemented by the computing device 106 and display device 108 to display the acquired image in accordance with the teachings of the present invention is illustrated in FIG. 5. It will be understood that any information generated by the first display 108 could also be generated by the second display 114 and/or printed by the printer 112. The graphical user interface illustrated in FIG. 5 includes a tab bar 502 along the top of the display 108, a group of operator controls 503 along the left side of the display 108, and the acquired image of the person's face 518 in the center of the display. A person of ordinary skill in the art will readily appreciate that many other arrangements of the user interface elements are possible.

Each type of display generated by the display device 108 is selectably arranged in the tab bar 502. Specifically, in this example, selection tabs are available for taking a picture 504, displaying the results of the population comparison 506, displaying the locations of one or more skin defects (508–514), and displaying the results of the worsening and/or improvement simulation 516. When the operator or the person being analyzed selects a tab in the tab bar 502 using the input device 212 in a known manner, the corresponding display is generated. These displays are shown in FIGS. 7, 10–14, and 16 and are discussed in detail below.

The operator and/or the person being analyzed may input data, select preferences, and command operation of the computing device 106 using the input device 212 and the operator controls 503. In this example, a text box 520 is available for inputting the person's name. The person's name may be used as an identifier on subsequent visits to retrieve data associated with previous analysis sessions from memory 202. The person's age may be entered in another text box 522. In such an instance, the person's age may be used to limit the population of people used when comparing the analysis results to averages (or other statistical parameters) for the population. Similarly, other text boxes (not shown) could be used to enter data associated with the person being analyzed. For example, the person's geographic location or ethnic origin could be used to limit the population data used when comparing the analysis results to the population.

Other operator controls include a "Take Picture" button 524, a "Mask" button 526, a slide control 528, preferences check boxes 530, and an "Analyze" button 532. The "Take Picture" button 524 initiates the computer controlled portion of the image acquisition process described above (see step 408 of FIG. 4). The "Mask" button 526 initiates the determination of sub-images (see step 304 of FIG. 3 and FIG. 6). The slide control 528 controls the size of one or more sub-images (described in detail below). The preferences check boxes 530 determine which of several skin attributes are to be analyzed (e.g., texture, wrinkles, pores, and/or spots) and whether a comparison to norms should be performed(e.g., a comparison to the average member of some population of people). The "Analyze" button 532 initiates the analysis process (see step 306 of FIG. 3 and FIG. 8).

Sub-Image Determination

Figure 6:
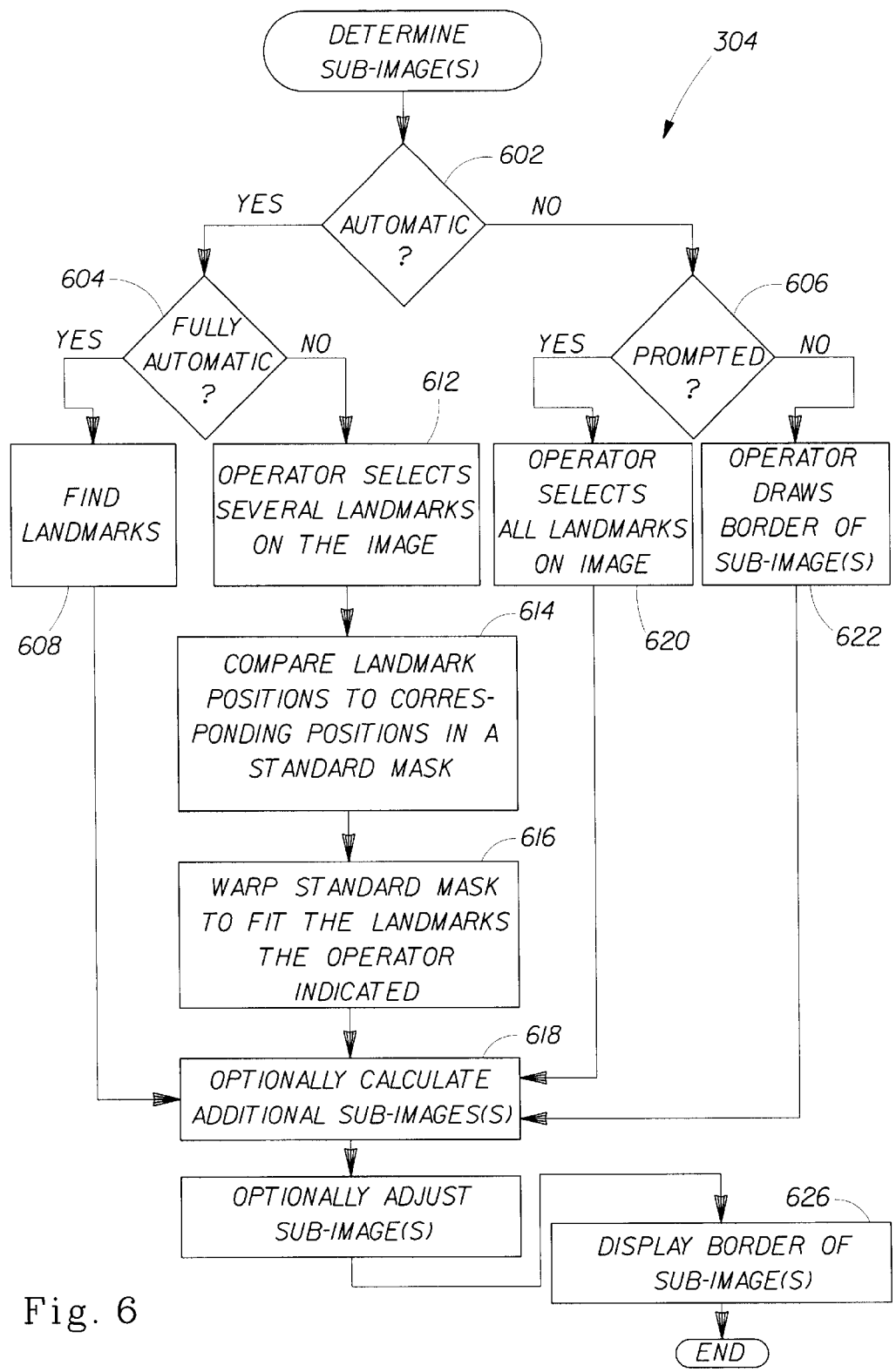
FIG. 6 is a detailed flow chart of a program that can be implemented by the computing device of FIG. 2 to determine sub-images in accordance with the teachings of the present invention.
Figure 7:
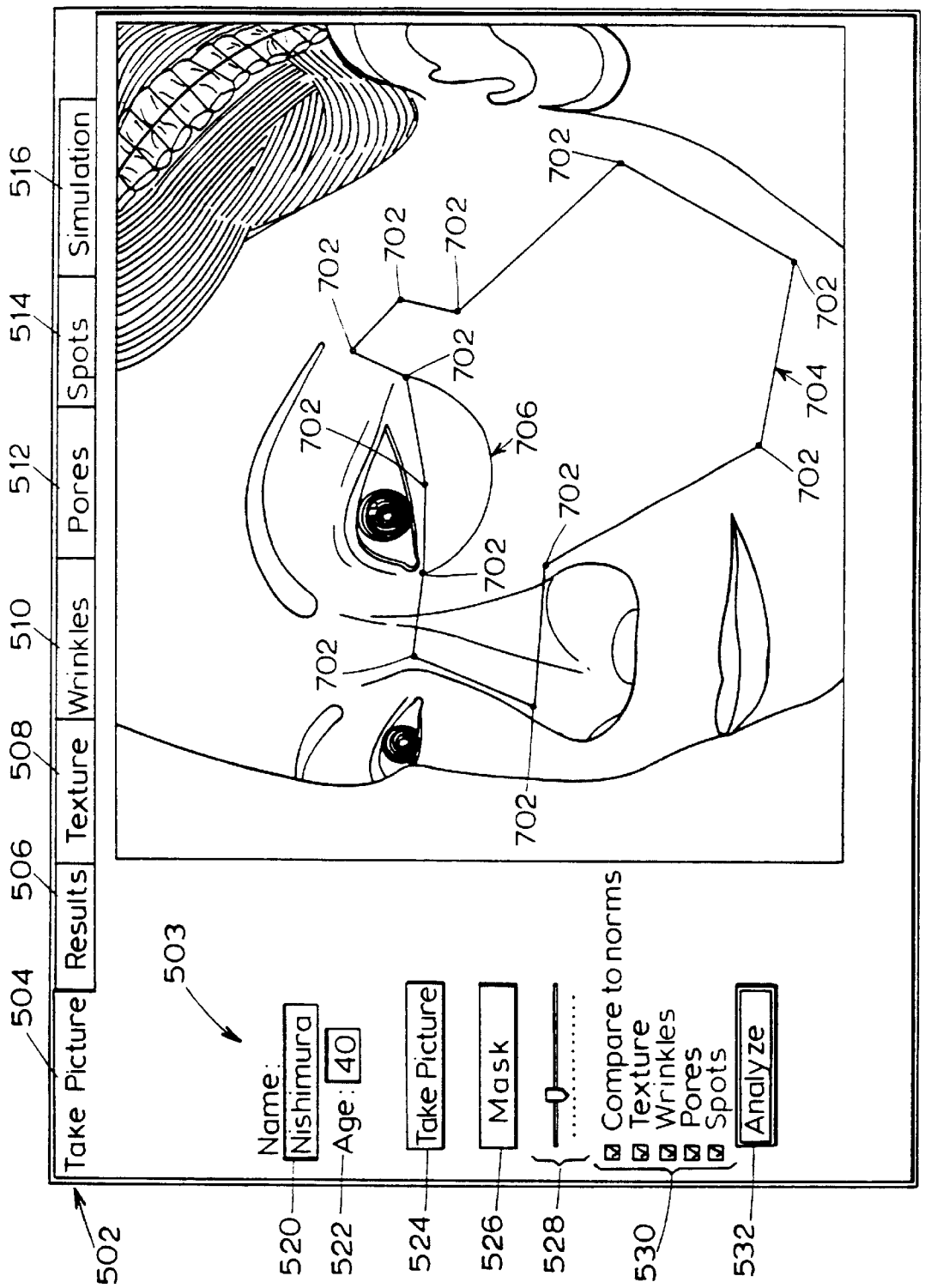
FIG. 7 is a line drawing of a graphical user interface that can be implemented by the computing device and display of FIG. 1 to display the location of sub-images in accordance with the teachings of the present invention.

A detailed flow chart of the program 304 (shown schematically in FIG. 3) that can be implemented by the computing device 106 to determine sub-images in accordance with the teachings of the present invention is illustrated in FIG. 6. In one embodiment, the steps are performed by the controller 200. A sub-image is a portion of the originally acquired image 518 upon which analysis will be performed. By eliminating a portion of the acquired image 518 from the analysis process, fewer errors occur. For example, by excluding consideration of the eyes and nose from the analysis process, an incorrect determination that a large discoloration of the skin is present is avoided (see sub image border 704 in FIG. 7). Four methods of determining the border of the sub-image are describe below. However, persons of ordinary skill in the art will readily appreciate that other methods may be used including combinations of the methods described herein.

The program 304 begins at step 602 where a decision is made to use automatic or manual sub-image determination. In one embodiment, this decision is made by the operator using the input device 212. In an alternate embodiment, the selection is determined by the controller 200. In such an instance, the controller 200 may analyze or partially analyze the image automatically, then, based on the results of that analysis, a decision is made by the controller 200 to use automatic or manual sub-image determination. For example, if the automatic sub-image determination includes a result indicative of a confidence level (e.g., how sure is it that it found the nose), and that confidence result is below some predetermined threshold, then the controller 200 may select manual sub-image determination.

If manual sub-image determination is selected, at step 606 a decision is made to use prompted or unprompted sub-image determination. This decision may be made by the operator using the input device 212. If unprompted sub-image determination is selected, at step 622 the operator draws a border 704 (see FIG. 7) for the sub-image using the input device 212 and the displayed image 518 in known manner. If prompted sub-image determination is selected, the controller 200 prompts the operator to select a series of landmarks 702 on the displayed image 518 (e.g., corner of the mouth, then corner of the nose, then corner of the eye, etc.). At step 620, the operator selects each of the landmarks 702 (see FIG. 7) for the sub-image using the input device 212 and the displayed image 518 in known manner. Subsequently, the controller 200 may draw in the sub-image border 704 by connecting the landmarks 702 in a known manner.

If automatic sub-image determination is selected, at step 604 a decision is made to use fully automatic or semi-automatic sub-image determination. This decision may be made by the operator using the input device 212. If semi-automatic sub-image determination is selected, at step 612 the operator selects several landmarks 702, but not all of the landmarks 702, for the sub-image using the input device 212 and the displayed image 518 in known manner. At steps 614 and 616, the controller 200 then determines the remaining landmarks 702 automatically by comparing the operator entered landmarks 702 to a predetermined landmark template (e.g., a standard mask) and interpolating the operator entered landmarks 702 using well known shape warping algorithms. For example, the remaining landmarks 702 may be calculated by taking the spatial difference vector (delta x, delta y) between the operator entered landmarks 702 and a standard mask for each of the operator entered landmarks 702. Then, the remaining landmarks 702 may be calculated using a bilinear interpolation of the spatial difference vectors and the x, y coordinates of the two closet operator entered landmarks 702. Subsequently, the controller 200 may draw in the sub-image border 704 by connecting the landmarks 702 (both operator entered landmarks 702 and automatically determined landmarks 702) in a known manner.

If fully automatic sub-image determination is selected, at step 608 the controller 200 determines all of the landmarks 702 for the sub-image automatically by searching for patterns in the digital image 518 indicative of predetermined landmarks. Many facial feature recognition algorithms are well known to persons of ordinary skill in the art. One such algorithm is detailed in M. Lievin, F. Luthon, "Lip Features Automatic Extraction", Proceedings of the 1998 IEEE International Conference on Image Processing, WA05.03, Chicago, October 1998, which is incorporated herein by reference.

Once the main sub-image is determined, additional sub-images may be determined at step 618. In one embodiment, an arc is drawn by the controller 200 between two of the landmarks 702 to define an "under eye" sub-image border 706 (see FIG. 7). At step 624, the operator may then adjust the size of the "under eye" sub-image by moving the slider control 528. For example, by moving the slider control 528 to the right, the arc defining the "under eye" sub-image is increased, and by moving the slider control 528 to the left, the arc defining the "under eye" sub-image is decreased. If not already performed by one or more steps described above, at step 626 the controller draws in the borders for all the sub-images.

In an alternate embodiment, a sub-image is electronically determined by comparing a plurality of color values of a plurality of pixels to a predetermined threshold indicative of skin color. This well known technique is described in M. H. Yang, N. Ahuja, "Detecting Human Faces in Color Images", Proceedings of the 1998 IEEE International Conference on Image Processing, MA05.02, Chicago, October 1998, which is incorporated here by reference. This technique is also described in R. Herpers, G. Verghese et. al., "An Active Stereo Vision System for Recognition of Faces and Related Hand Gestures", Proceedings of the Second International Conference on Audio and Video—Based Person Authentication (AVBPA99), Washington DC, Mar. 23–24, 1999, which is incorporated here by reference.

Sub-Image Analysis

Figure 8:
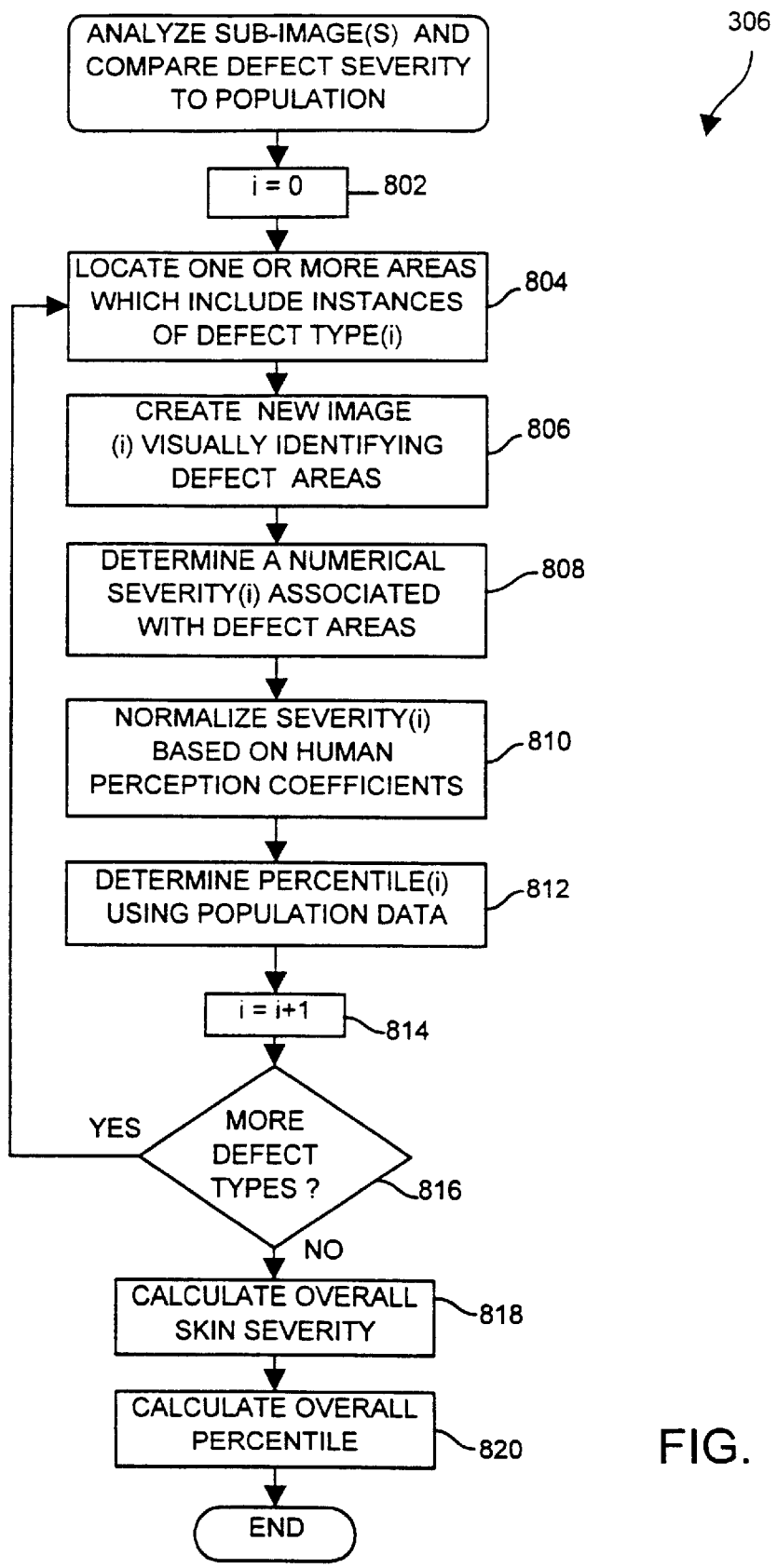
FIG. 8 is a detailed flow chart of a program that can be implemented by the computing device of FIG. 2 to analyze the sub-images to locate defect areas and compare the severity of the defect areas to an average skin severity of a population of people in accordance with the teachings of the present invention.

Once the sub-image(s) are determined, they are analyzed. A detailed flow chart of the program 306 (shown schematically in FIG. 3) that can be implemented by the computing device 106 to analyze the sub-images to locate defect areas and compare the severity of the defect areas to an average skin severity of a population of people, in accordance with the teachings of the present invention, is illustrated in FIG. 8. In one embodiment, the steps are performed by the controller 200. Defect areas are areas in the sub-image which meet certain criteria (e.g., a red spot). The severity of a particular instance of a defect is an estimation of the degree to which humans perceive one defect as being "worse" than another. For example, a large red spot is considered more severe than a small red spot. Many different defect types may be located. For example, skin elasticity features such as wrinkles and/or fine lines may be located. Skin smoothness, skin texture, follicular pores, inflamed red spots such as acne, hyperpigmented spots such as senile lentigenes, nevi, freckles, as well as many other skin defects may also be located using a variety of known algorithms. Examples of these algorithms are described in Japanese Patent Document 95-231883, "Skin Surface Analysis System and Skin Surface Analysis Method," PCT Document WO 98/37811, "Systems and Methods for the Multispectral Imaging and Characterization of Skin Tissue," and U.S. Pat. No. 5,016,173, "Apparatus and Method for Monitoring Visually Accessible Surfaces of the Body," each of which is incorporated here by reference.

The program 306 begins at step 802 where an index variable is initialized to zero. The purpose of the index variable is to keep track of which type of skin defect is being analyzed. If only one defect type is being analyzed, the index variable may be eliminated. At step 804 a plurality of areas in the sub-image containing the current defect type are located. For example, if the sub-image contains six red spots (as defined by a known red spot detection algorithm) then six locations in the sub-image are determined. Each location may be identified using a single set of geometric coordinates specifying the approximate center of the located defect, or, each location may be identified by a set of geographic coordinates covering a region affected by the current defect type.

At step 806, the controller 200 creates a new digital image based on the original digital image of the face of the person and the location of the defect areas (see FIGS. 11–14). The new digital image visually identifies to the user the plurality of defect areas located in the original digital image by electronically altering the color of a plurality of pixels substantially in the area containing the skin defect (i.e., on or around the defect area) to at least one color visually distinct from the skin color of the first digital image. For example, the skin color of each pixel in the defect area may be shifted to a similar shade of blue to create a transparent overlay. In another example, a green circle could be drawn around each of the six red spots to visually identify the location of the six red spots.

At step 808, the controller 200 determines a numerical severity associated with the defect areas. In one embodiment, a color content associated with the defect area is subtracted from the color content of the area immediately surrounding the defect area. For example, if the pixels used to create a red spot have a red content of 60% and the pixels used to create the surrounding skin color have a red content of 10%, then the numerical severity associated with the red spot defect in this example may be determined to be 50. In another embodiment, the number of geometric coordinates necessary to cover the defect area is the numerical severity. For example, if a detected pore covers 30 pixels, then the numerical severity associated with that pore may be determined to be 30. The severity of multiple instances of a particular defect type may be aggregated. For example, multiple severities may be summed or averaged.

At step 810, the controller 200 may normalize the aggregated severity based on human perception coefficients. For example, if it is determined in a clinical study that red spots are twice as noticeable as brown spots, the aggregated severity associated with the red spot analysis may be doubled. Alternatively, in this example, the aggregated brown spot severity may be halved. Of course, a person of ordinary skill in the art will readily appreciate that more than two defect types may be normalized.

At step 812, the controller may determine a percentile for the normalized severity using data associated with a certain population of people. The population data used may be specific to the analyzed person's age, geographic location, ethnic origin, or any other factor. For example, if 55% of a sample group of people in the analyzed person's age group had a normalized severity for the current defect type below the analyzed person's severity, and 45% of the sample group had a severity above the analyzed person's severity, then a percentile of 55 or 56 is determined.

At step 814 the controller 200 increments the index, and at step 816 the controller 200 checks if there are more defect types to be processed. If there are more defect types, control returns to step 804, and the process is repeated. Each time through the loop defined by steps 804–816, the controller 300 may use a different algorithm for defect location, create a new image identifying the defect areas, use a different algorithm for severity calculation, use different coefficients for normalizing, and use different population data when determining the percentile (see FIGS. 10–14).

When there are no more defect types to process, the controller 200 may calculate an overall skin severity and an overall percentile at step 818 and step 820 respectively. The overall skin severity may be an aggregation of the plurality of individual skin defect severities. For example, the severities determined by the iterations of step 808 may be summed or averaged. The overall percentile may be calculated as described above for the individual skin defect percentiles; however, a different data set representing overall severities of a population of people may be used. Again, the population data may be selected based on the analyzed person's demographics.

In addition to an overall skin severity based on the aggregation of individual skin defect severities, one or more overall skin characteristics may be determined. An overall skin characteristic may not depend on the detection of any individual skin defects. For example, an overall smoothness/roughness magnitude may be determined. Such a determination may include certain skin defects (e.g., analyze entire image or sub-image) or it may exclude certain skin defects (e.g., do not analyze pixels in the hyper-pigmentation defect areas).

Several methods for determining an overall skin severity are well known to persons of ordinary skill in the art. For example, surface area density may be determined. Surface area density is a measurement of the "total surface area" divided by the pixel count. If the digital image is considered a topographical map, the "total surface area" may be calculated by summing the areas of the "tops" and the "sides" of each pixel, where brighter areas are considered taller. A single bright pixel with a value of "pixel-value" in a zero surround would have a surface area given by (pixel-width*pixel-height+2*pixel-width*[pixel-value]+2*pixel-height*[pixel-value]) where pixel-width and pixel-height are the distances between pixels in the x and y direction respectively. This method is discussed in detail in Calum MacAulay and Branko Palcic, "Fractal Texture Features Based on Optical Density Surface Area", Analytical and Quantitative Cytology and Histology, vol. 12, no. 6, December 1990, which is incorporated here by reference.

Another method for determining an overall skin severity, well known to persons of ordinary skill in the art, is a fractal texture measurement. Fractal dimensions characterizes how a surface changes when measured at different resolutions. Fractal texture is estimated from 2+((log 10(SurfaceArea-log 10(SurfaceArea3×3))/log 10(2)) where SurfaceArea is an estimate of the surface area of the image or sub-image and SurfaceArea3×3 is an estimate of the surface area at a 3×3 neighborhood resolution. This method is discussed in detail in MacAulay, Calum and Palcic, Branko, "Fractal Texture Features Based on Optical Density Surface Area", Analytical and Quantitative Cytology and Histology, vol. 12, no. 6, December 1990, and Peleg, Shmuel, et. al., "Multiple Resolution Texture Analysis and Classification", IEEE Transactions on Pattern Analysis and Machine Intelligence, VOL. PAMI-6, NO. 4, July 1984, both of which are incorporated here by reference.

Yet another method for determining an overall skin severity, well known to persons of ordinary skill in the art, is pixel intensity variance. Rough skin areas typically comprise both bright and dark pixels, leading to a human impression of uneven skin tone. Pixel intensity variance can be calculated for some or all the pixels in the image or sub-image. Higher variance indicates rougher skin. Often, images and sub-images have a lighting gradient, in which case the variance calculation captures primarily the unevenness of the lighting rather than the unevenness of the skin. Erroneous results caused by lighting gradients can be handled in at least two ways. First, if the lighting gradient is fixed and known (e.g., the imaging equipment is calibrated using a flat monotone surface), a well known technique called "background correction" can be used to eliminate the lighting variance. Second, the variance can be calculated for a local region of the image where the lighting gradient is small or negligible. For example, a 21×21 pixel sub-region centered on a pixel in the image being analyzed may be used, and the variance within that sub-region may then be written to the same pixel location in a new image. By repeating this process for a plurality of pixels in the original image, a "variance image" is created. The mean intensity of the variance image is an accurate estimate of the local variance in the original image.

Display Analysis Results

Figure 9:
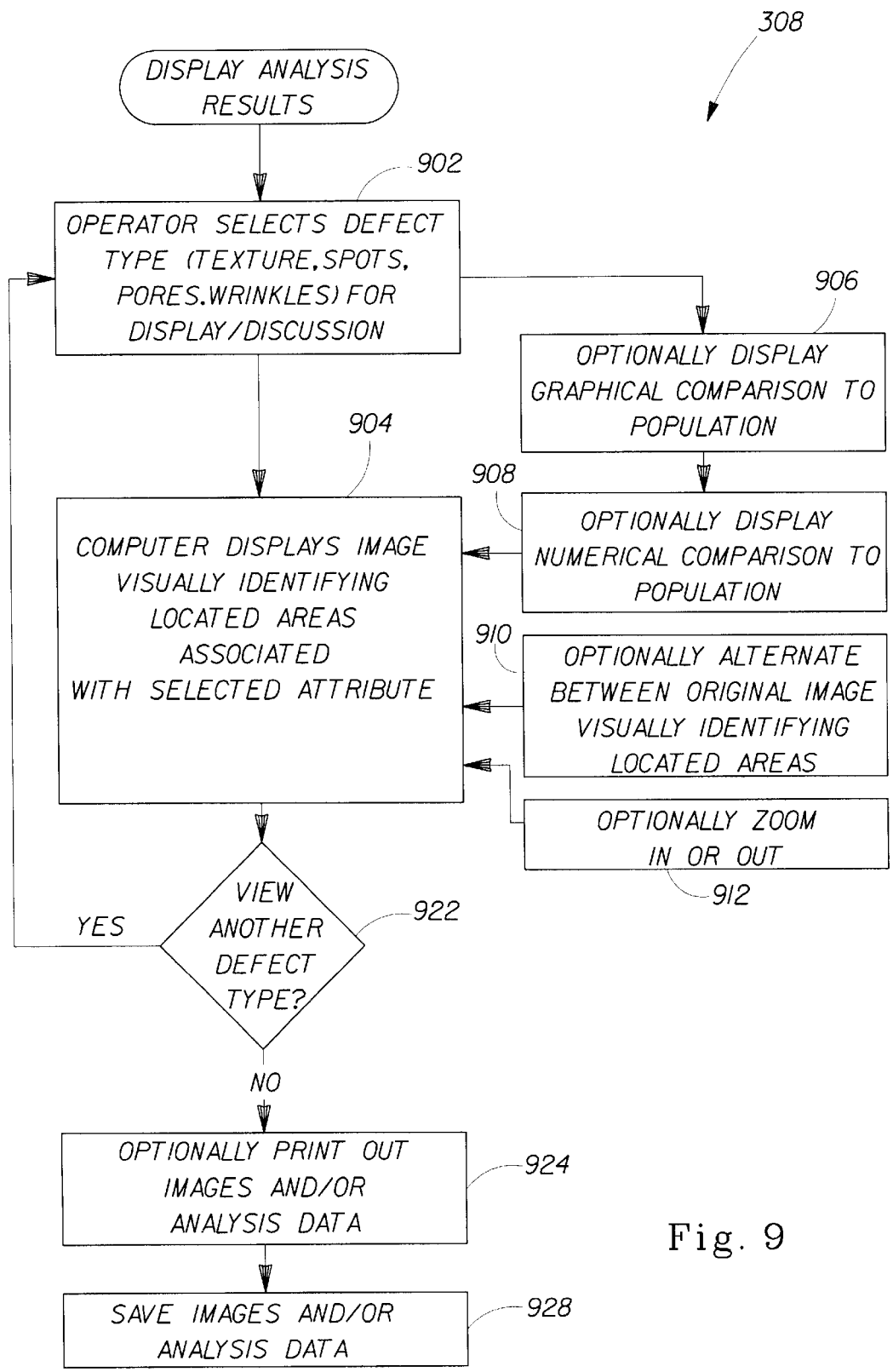
FIG. 9 is a detailed flow chart of a program that can be implemented by the computing device of FIG. 2 to display analysis results in accordance with the teachings of the present invention.
Figure 10:
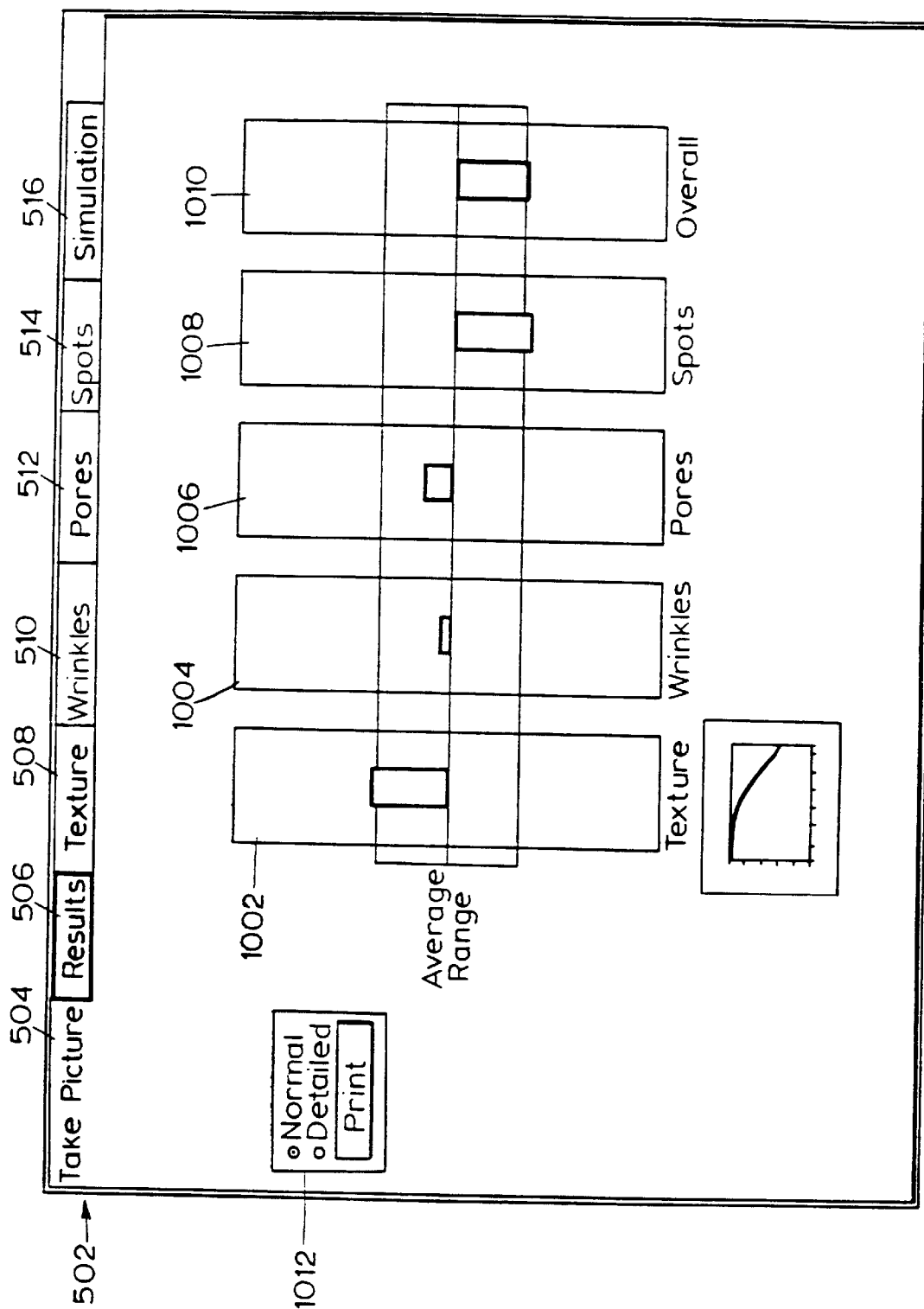
FIG. 10 is a line drawing of a graphical user interface that can be implemented by the computing device and display of FIG. 1 to display a graphical comparison between a particular skin severity and an average skin severity associated with a population of people in accordance with the teachings of the present invention.
Figure 11:
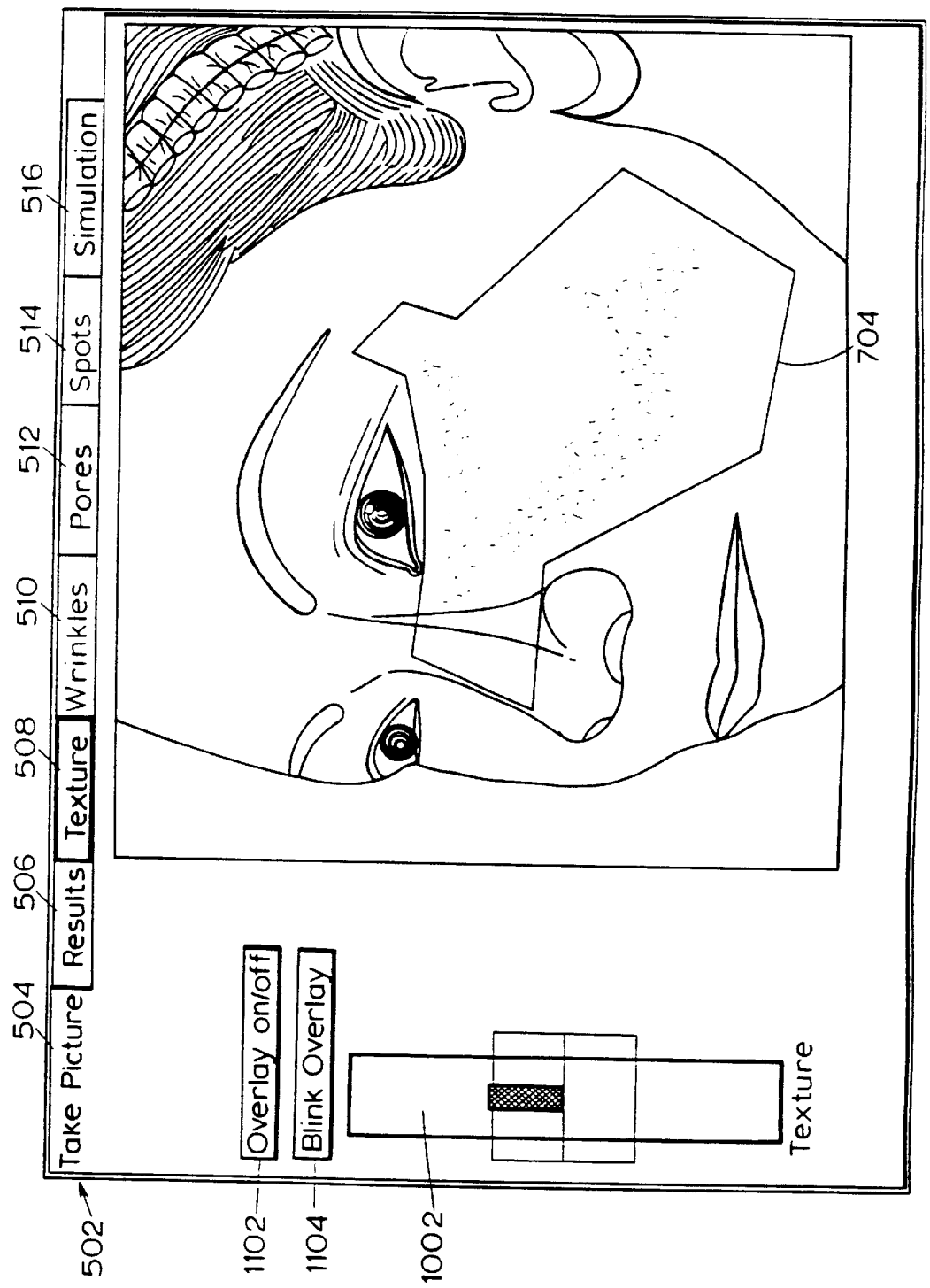
FIGS. 11–14 are line drawings of graphical user interfaces that can be implemented by the computing device and display of FIG. 1 to display the location of a plurality of defects in accordance with the teachings of the present invention.
Figure 12:
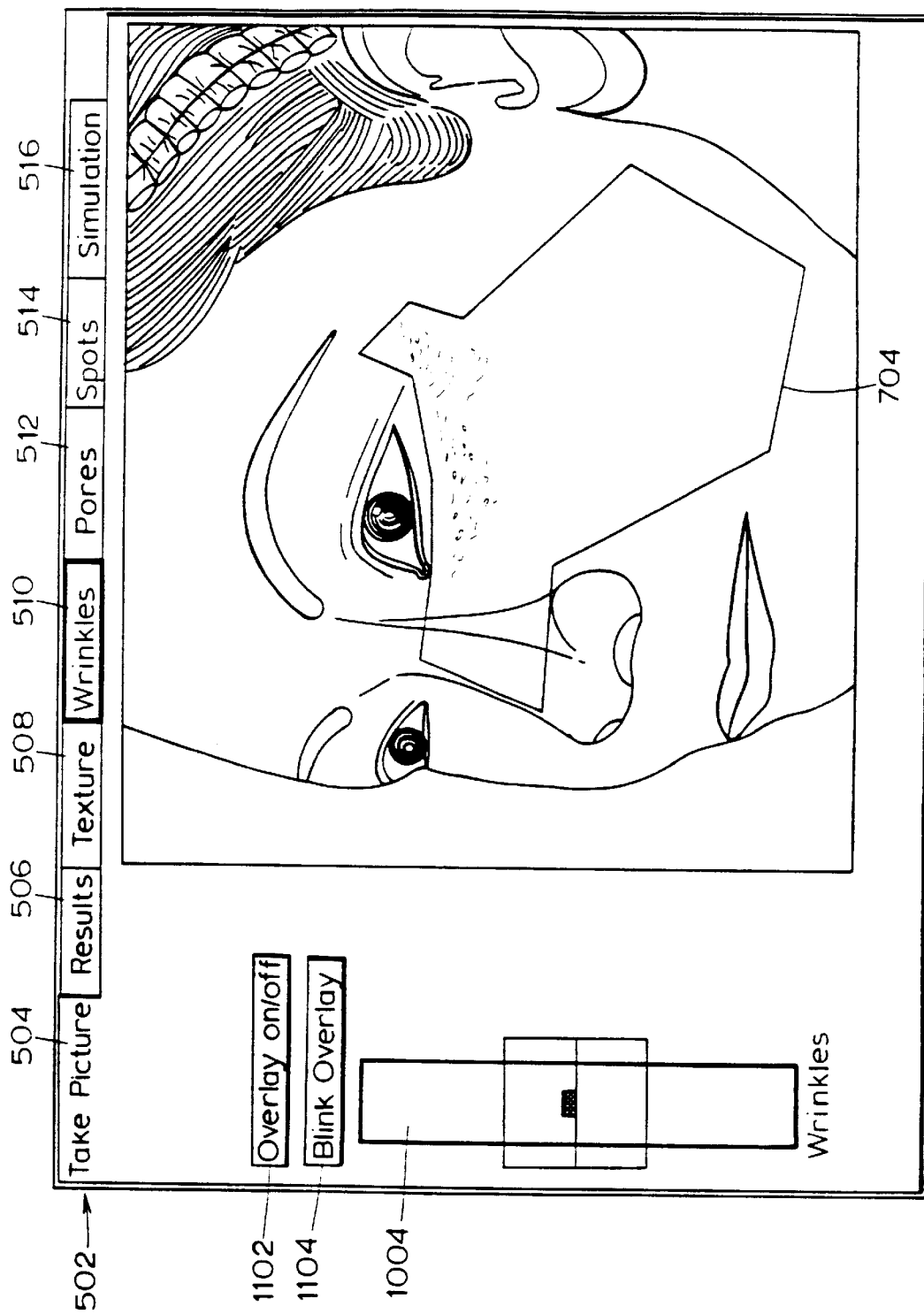
Figure 13:
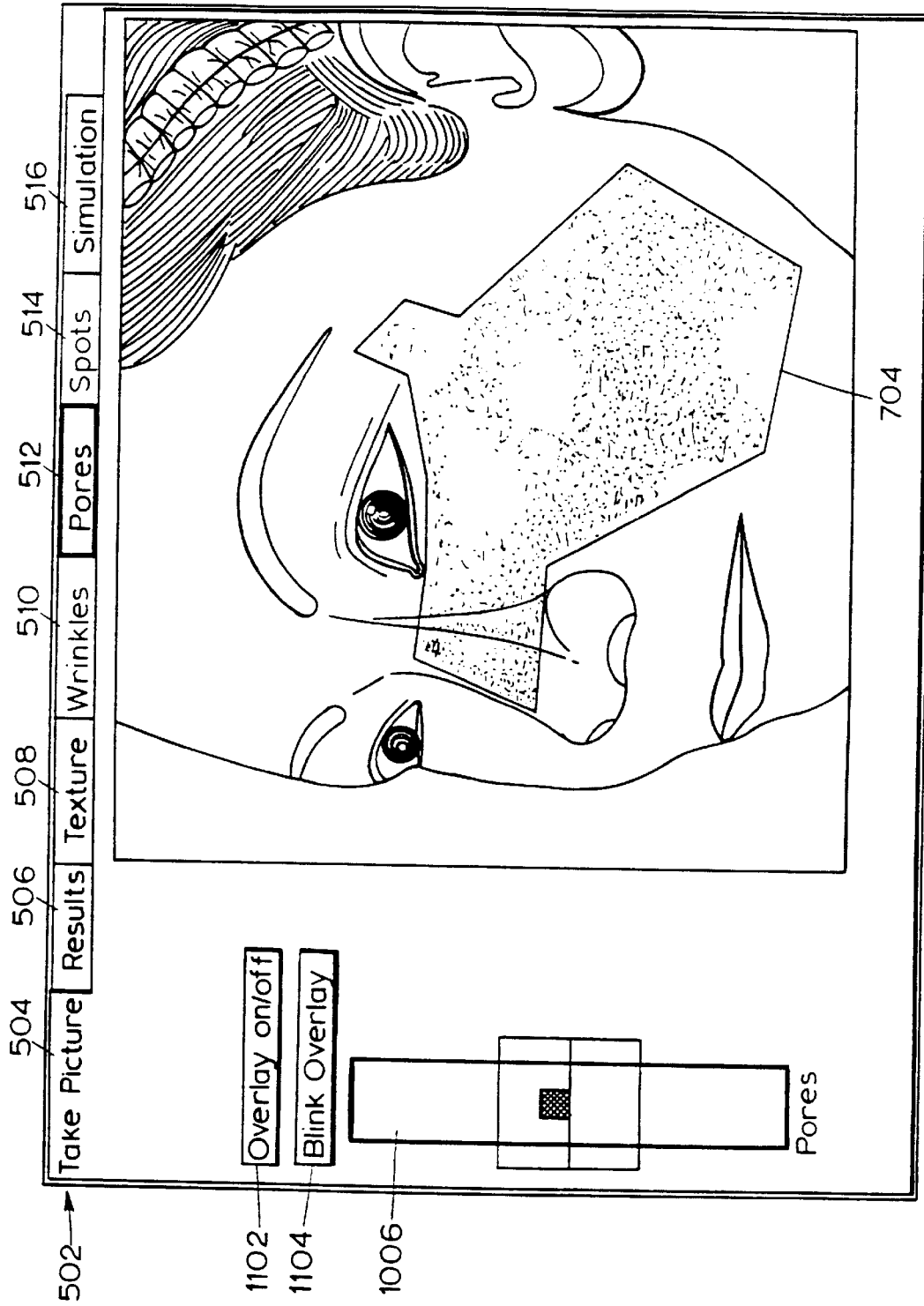
Figure 14:
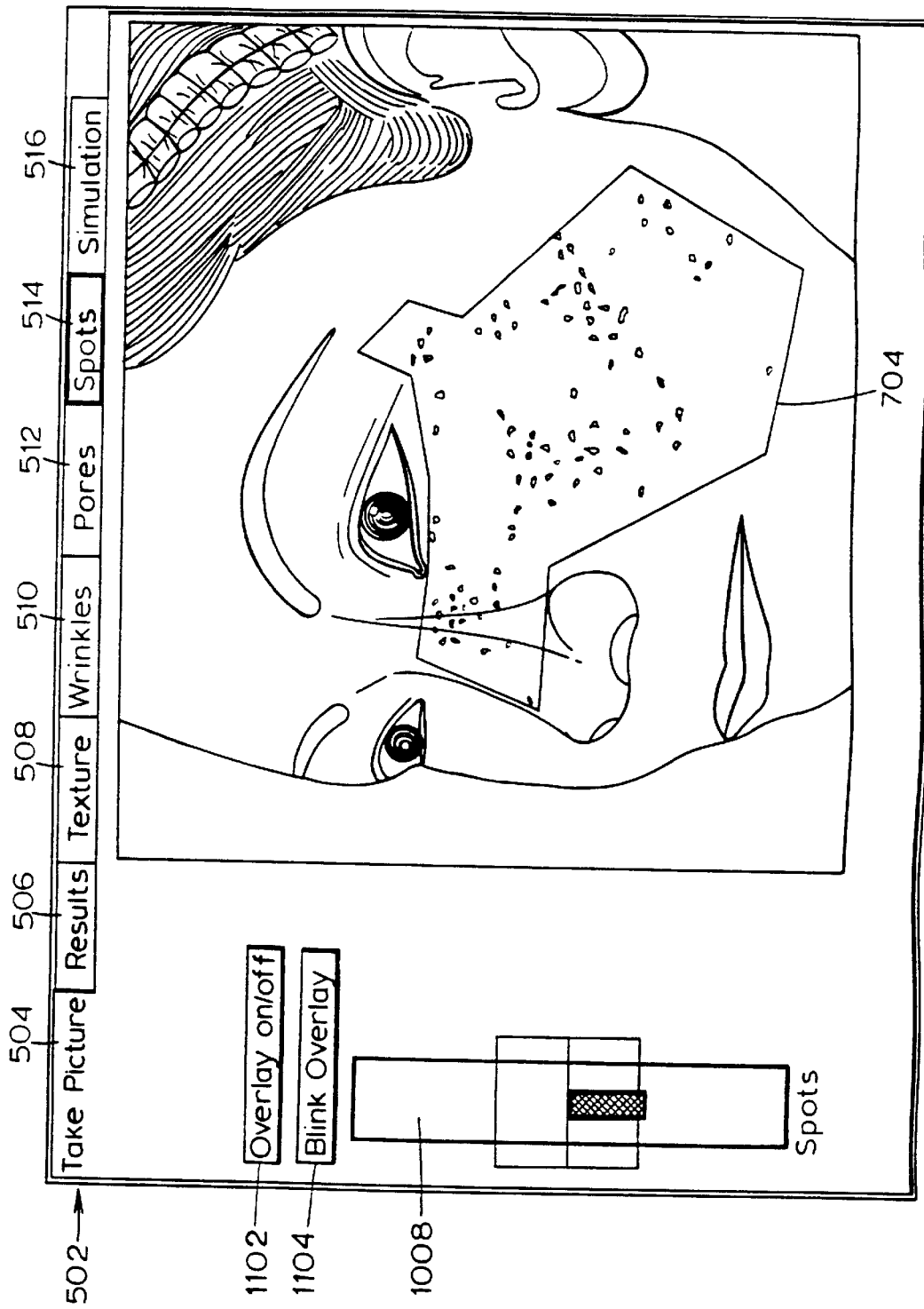

Once the sub-images are analyzed, they may be outputted. Outputting an image includes any form of computer output. For example, the image may be transmitted via the network 222, displayed by the printer 112, and/or displayed by one or more displays 108, 114. A detailed flow chart of the program 308 (shown schematically in FIG. 3) that can be implemented by the computing device 106 to display analysis results in accordance with the teachings of the present invention is illustrated in FIG. 9. In one embodiment, the steps are performed by the controller 200. The program 308 allows the operator or the analyzed person to select different images created in step 806 for viewing. The program also allows the operator or the analyzed person to select the various severities and percentiles calculated by program 306 for viewing.

The program begins at step 902, where the operator selects a defect type for display and discussion. Selection may be performed by using the input device 212 to select a defect type from the tab bar 502 along the top of the display 108. In this example, four defect types were analyzed, corresponding to the four tab bar choices of texture 508, wrinkles 510, pores 512, and spots 514 (see FIG. 11). Once a selection is made, at step 904 the controller 200 causes the main display 108 and/or the optional display 114 to generate the image visually identifying the defect areas created in step 806 (see FIGS. 11–14). At step 922, the operator may choose to view another defect type by selecting another tab bar choice 508, 510, 512, 514.

When viewing the images visually identifying the defect areas, the operator may choose to hide the electronic alterations identifying each defect area by selecting an "Overlay on/off" button 1102. Similarly, at step 910, the operator may command the controller 200 to repeatedly alternate between hiding and showing the electronic alterations by selecting a "Blink Overlay" button 1104. By alternating between the original image 518 and the image identifying the defect areas, human comprehension of the location of the plurality of defect areas is increased.

In addition to the viewing the images identifying the defect areas, at step 906 the operator may select the results tab 506 to view a graphical comparison of the analyzed person's defect severities and percentiles to an average for a similar population. In the example shown in FIG. 10, a bar chart is displayed. However, a person of ordinary skill in the art will readily appreciate that many other types of graphical comparison may be used. In the bar chart shown, a bar projecting above a line representing the average for the selected population represents a skin severity that is better than normal. A bar projecting below the "average line" represents a skin severity that is below normal. Larger bars correspond to greater magnitudes. At step 908 the operator may choose to view the numerical results associated with the graphical display by selecting the "Detailed" option in a control box 1012 located on the display. When the "Detailed" option is selected, the numerical results may be shown in addition to the graphical results. For example, the numerical results could be superimposed near each bar in the bar graphs 1002–1010.

At step 924 the operator may choose a "Print" button located in the control box 1012. In this embodiment, selection of the "Print" button causes the controller 200 to instruct the printer 112 to generate one or more graphical displays, such as the images visually identifying the defect areas and the comparison chart. At step 928 the data associated with the analysis may be saved to memory 202. In one embodiment, the analyzed person's name is used as an identifier on subsequent visits to retrieve data associated with previous analysis sessions from memory 202.

Generate Simulated Image

Once the analysis results are displayed, the controller 200 and the display 108 may generate a simulated image showing an improvement and/or worsening to the defect areas. Simulating worsening may be useful when the operator is recommending a treatment using a product which prevents skin degradation to show the analyzed person the potential affects if she fails to take precautionary measures. Simulating improvements may be useful when the operator is recommending a treatment using a product which eliminates and/or hides skin defects to show the analyzed person the potential benefits of the product(s). Further, the controller 200 may cause the display 108 (or other output device) to generate a product recommendation. For example, a look-up table may be stored in 202 which includes different types of defects and magnitudes of those defects cross referenced to cosmetic products and/or treatments which help eliminate those defects, help prevent those defects, and/or help hide those defects.

Figure 15:
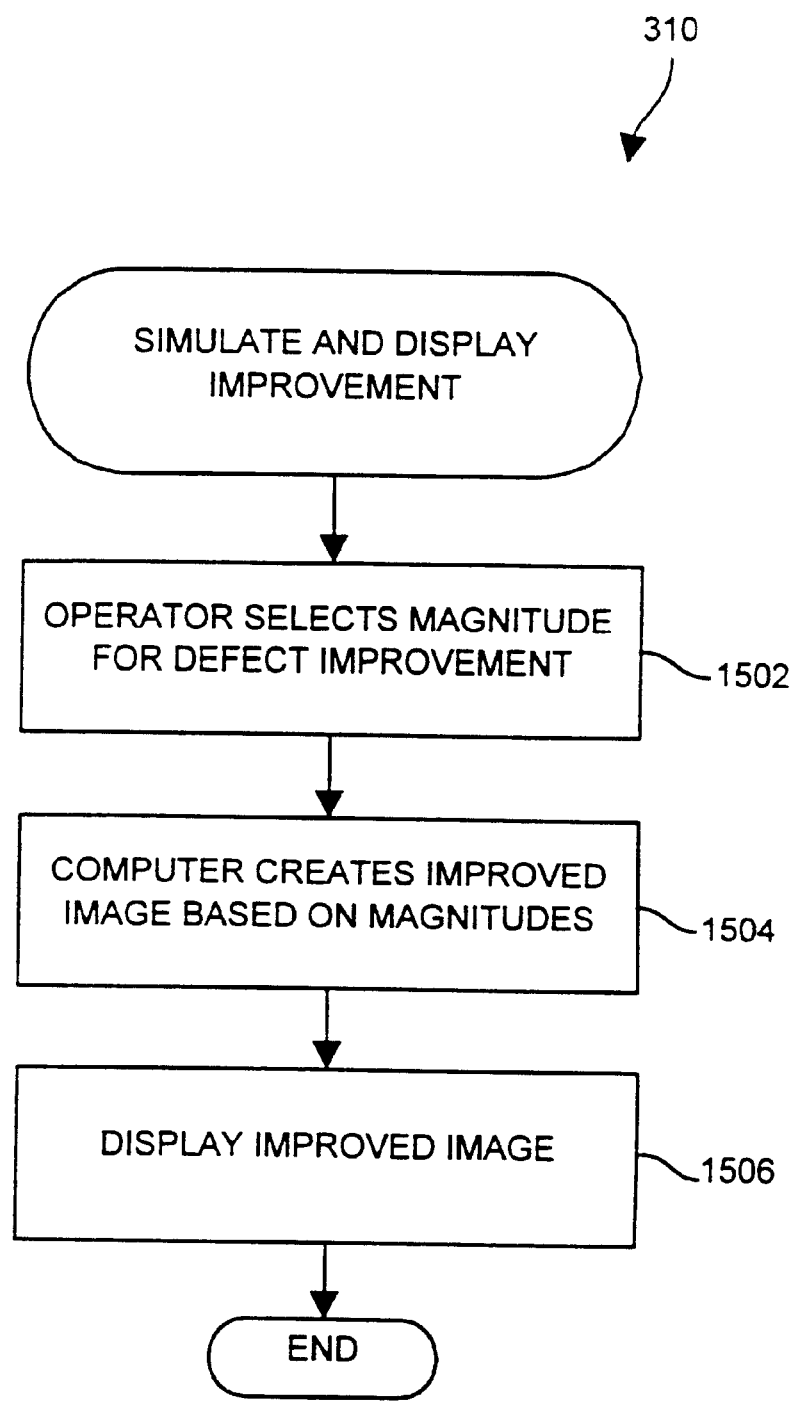
FIG. 15 is a detailed flow chart of a program that can be implemented by the computing device of FIG. 2 to simulate and display improvements to the located defect areas in accordance with the teachings of the present invention.
Figure 16:
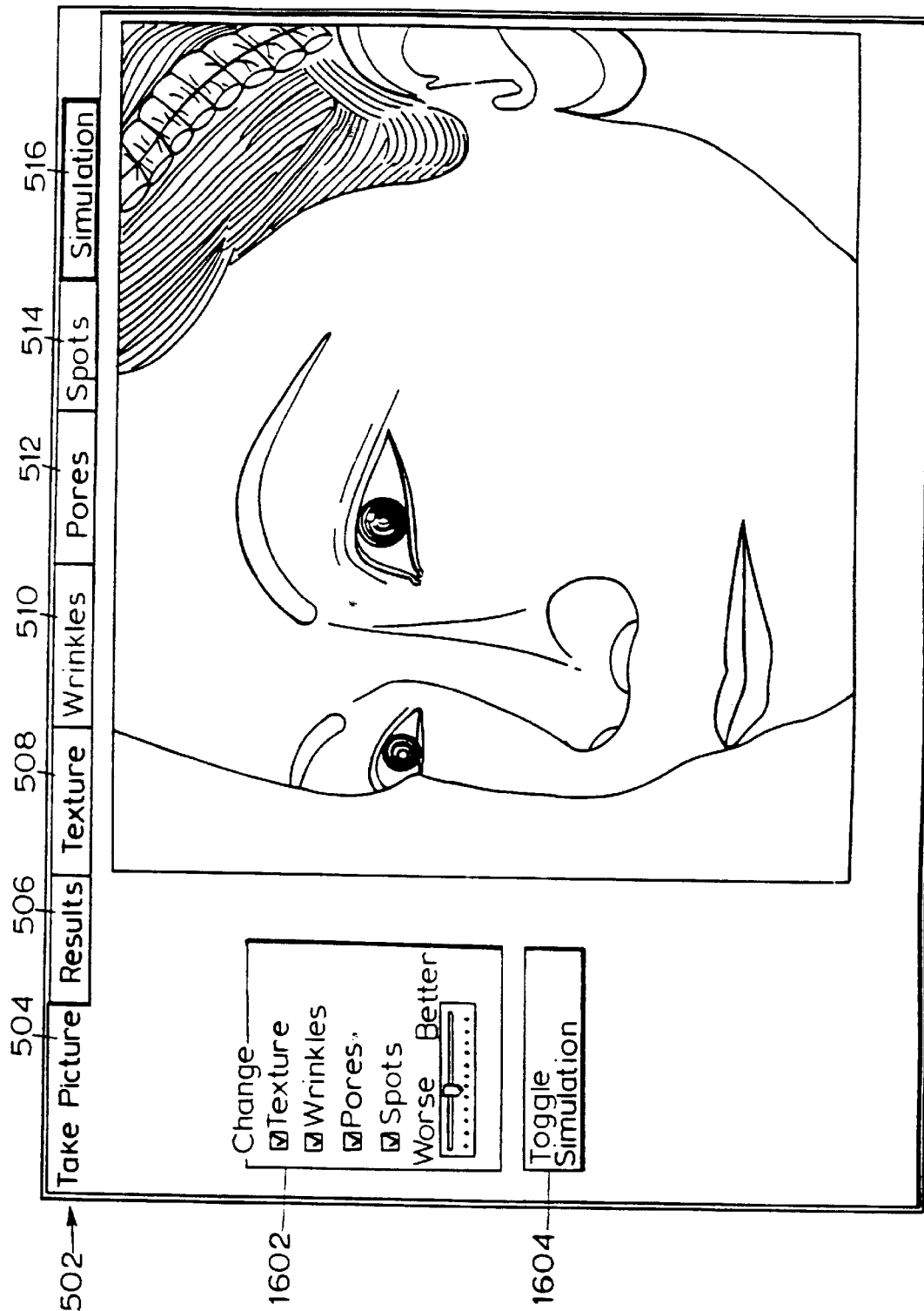
FIG. 16 is a line drawing of a graphical user interface that can be implemented by the computing device and display of FIG. 1 to display the results of the simulated improvement and/or worsening of the located defect areas in accordance with the teachings of the present invention.

A flow chart of the program 310 (shown schematically in FIG. 3) that can be implemented by the computing device 106 to simulate and display improvements to the located defect areas in accordance with the teachings of the present invention is illustrated in FIG. 15. In one embodiment, the steps are performed by the controller 200. The program begins at step 1502 where the operator enters a magnitude for defect improvement via the input device 212. For example, if the overall percentile is determined to be the fortieth percentile, then the operator may choose to simulate an improvement of ten percentile points to create an "average" fiftieth percentile image.

At step 1504 the controller 200 creates an improved image based on the original image 518, the locations of the defect areas, and the magnitude entered at step 1502. Many facial simulation and morphing algorithms are well known. Generally, simulating an improvement to a defect area comprises modifying the color of the plurality of pixels in the defect area to more closely match the color of pixels in the area surrounding the defect area. Examples of morphing algorithms may be found in Japanese Patent Document 95-100126, "Simulation of Facial Wrinkles," Japanese Patent Document 98-065928, "Image Processing Method," and U.S. Pat. No. 4,276,570, "Method and Apparatus for Producing an Image of a Person's Face at a Different Age," each of which is incorporated here by reference. Finally, at step 1506, the improved image is displayed (see FIG. 16).

Defect types (e.g., texture, wrinkles, pores, spots, etc.) may be selectively included in the improved image via a "Change" control 1602 which includes a group of check boxes. In addition, the "Change" control 1602 allows the operator and/or the user to change the magnitude of the improvement and/or allows the operator and/or the user to choose to view a worsening of the image. For example, by sliding a control to the right, the defects may be modified to be more similar to the surrounding skin; while, sliding the control to the left has the affect of worsening the image. A "Toggle Simulation" button 1604 may allow the operator and/or the user to switch between displaying the original digital image 518 and displaying the improved or worsened digital image. Displaying the original digital image 518 and displaying the improved digital image may also be repeatedly alternated to increase human comprehension of the simulated improvement.

In summary, persons of ordinary skill in the art will readily appreciate that a skin analysis system and methods have been provided. Systems implementing the teachings of the present invention can quickly identify skin defects in a user friendly manner thereby allowing an operator to recommend cosmetic products and/or medical treatments and to simulate an improvement and/or a worsening of the skin.

The foregoing description has been presented for the purposes of illustration and description. It is not intended to be exhaustive or to limit the invention to the precise form disclosed. Many modifications and variations are possible in light of the above teachings. It is intended that the scope of the invention be limited not by this detailed description, but rather by the claims appended hereto.

What is claimed is:

1. A method for locating one or more visual skin defects of a portion of a person, comprising:

acquiring a first digital image of the portion of the person;

electronically analyzing the first digital image of the portion of the person to locate an area containing a skin defect;

determining a first numerical severity associated with the area containing the skin defect; and generating a comparison between the first numerical severity and a predetermined value associated with a population of people.

2. A method as defined in claim 1, wherein the predetermined value associated with the population of people is one of the group consisting of (a) an age specific value, (b) a geographic specific value, and (c) an ethnic specific value.

3. A method as defined in claim 1, further comprising storing the first numerical severity associated with the area containing the skin defect for the purpose of tracking a plurality of skin defect severities associated with the person over time.

4. A method as defined in claim 1, further comprising:
electronically creating a second digital image visually identifying the area containing the skin defect; and
displaying the second digital image.

5. A method as defined in claim 4, further comprising:
electronically creating a third digital image simulating an improvement to the area containing the skin defect by electronically altering the color of a plurality of pixels in the area containing the skin defect; and
displaying the third digital image.

6. A method as defined in claim 4, further comprising the step of displaying the first digital image of the portion of the person, wherein the step of displaying the first digital image of the portion of the person and the step of displaying the third digital image, simulating an improvement to the area containing the skin defect, are repeatedly alternated.

7. A method as defined in claim 4, further comprising:
electronically creating a third digital image simulating a worsening to the area containing the skin defect by electronically altering the color of a plurality pixels in the area containing the skin defect; and
displaying the third digital image.

8. A method as defined in claim 4, further comprising the step of displaying the first digital image of the portion of the person, wherein the step of displaying the first digital image and the step of outputting the second digital image are repeatedly alternated.

9. A method as defined in claim 4, further comprising:
identifying a plurality of landmarks located on the first digital image of the portion of the person; and
electronically determining a sub-image of the first digital image of the portion of the person based on the plurality of landmarks,
wherein the step of electronically analyzing the first digital image is limited to the sub-image.

10. A method as defined in claim 4, comprising the step of electronically determining a sub-image of the first digital image of the portion of the person by comparing a plurality of color values of a plurality of pixels to a predetermined threshold indicative of skin color, wherein the step of electronically analyzing the first digital image is limited to the sub-image.

11. A method as defined in claim 4, wherein the first skin defect comprises one of the group consisting of (a) wrinkles, (b) fine lines, (c) smoothness,(d) texture, (e) follicular pores, (f) red spots, (g) hyperpigmentation, and (h) brown spots.

12. A method as defined in claim 1, further comprising electronically analyzing the first digital image of the face of the person to determine an overall skin characteristic associated with the digital image of the face of the person.

13. An apparatus adaoted to perform the method of claim 1.

14. A tangible medium storing program instructions adapted to perform the method of claim 1.

15. A method for locating one or more visual skin defects of a portion of a person, comprising:
acquiring a first digital image of the portion of the person;
electronically analyzing the first digital image of the portion of the person to locate an area containing a skin defect;
determining a first numerical severity associated with the area containing the skin defect; and
comparing the first numerical severity with a second numerical severity, wherein the second numerical severity is associated with the person after a skin treatment.

16. A method as defined in claim 15, further comprising:
electronically creating a third digital image simulating an improvement to the area containing the skin defect by electronically altering the color of a plurality of pixels in the area containing the skin defect; and
displaying the third digital image.

17. A method as defined in claim 15, further comprising the step of displaying the first digital image of the portion of the person, wherein the step of displaying the first digital image of the portion of the person and the step of displaying the third digital image, simulating an improvement to the area containing the skin defect, are repeatedly alternated.

18. A method as defined in claim 15, further comprising:
electronically creating a third digital image simulating a worsening to the area containing the skin defect by electronically altering the color of a plurality pixels in the area containing the skin defect; and
displaying the third digital image.

19. A method as defined in claim 15, further comprising the step of displaying the first digital image of the portion of the person, wherein the step of displaying the first digital image and the step of outputting the second digital image are repeatedly alternated.

20. A method as defined in claim 15, further comprising storing the first numerical severity associated with the area containing the skin defect for the purpose of tracking a plurality of skin defect severities associated with the person over time.

21. A method as defined in claim 15, further comprising:
identifying a plurality of landmarks located on the first digital image of the portion of the person; and
electronically determining a sub-image of the first digital image of the portion of the person based on the plurality of landmarks,
wherein the step of electronically analyzing the first digital image is limited to the sub-image.

22. A method as defined in claim 15, further comprising the step of electronically determining a sub-image of the first digital image of the portion of the person by comparing a plurality of color values of a plurality of pixels to a predetermined threshold indicative of skin color, wherein the step of electronically analyzing the first digital image is limited to the sub-image.

23. A method as defined in claim 15, wherein the first skin defect comprises one of the group consisting of (a) wrinkles, (b) fine lines, (c) smoothness,(d) texture, (e) follicular pores, (f) red spots, (g) hyperpigmentation, and (h) brown spots.

24. A nethod as defined in claim 15, further comprising:
electronically creating a second digital image visually identifying the area containing the skin defect; and
displaying the second digital image.

25. A method as defined in claim 15, further comprising electronically analyzing the first digital image of the face of the person to determine an overall skin characteristic associated with the digital image of the face of the person.

26. A method as defined in claim 15, further comprising the step of generating a comparison between the first numerical severity and a predetermined value associated with a population of people.

27. A method as defined in claim 26, wherein the predetermined value associated with the population of people is one of the group consisting of (a) an age specific value, (b) a geographic specific value, and (c) an ethnic specific value.

28. An apparatus adapted to perform the method of claim 15.

29. A tangible medium storing program instructions adapted to perform the method of claim 15.

30. A method for locating a plurality of visual skin defects associated with a face of a person, comprising:

acquiring a first digital image of the face of the person, the first digital image having a size and a skin color;

identifying a first plurality of landmarks located on the first digital image of the face of the person, wherein at least one of the landmarks is selected from the group comprising (a) a corner of an eye in the first digital image, (b) a corner of a nose in the first digital image, and (c) a corner of a mouth in the first digital image;

electronically determining a sub-image of the first digital image of the face of the person based on the first plurality of landmarks; and electronically analyzing the sub-image of the first digital image of the face of the person to locate a plurality of defect areas, wherein each defect area contains a visual skin defect and each defect area has a size that is less than about 10% of the size of the first digital image of the face of the person.

31. A method as defined in claim 30, wherein the step of identifying the first plurality of landmarks located in the first digital image of the face of the person comprises selecting the positions of the first plurality of landmarks by activating an input device while a cursor is displayed on a display device at each of the landmarks in the first plurality of landmarks.

32. A method as defined in claim 30, wherein the step of identifying the first plurality of landmarks located in the first digital image of the face of the person comprises:

selecting the positions of a second plurality of landmarks by activating an input device while a cursor is displayed on a display device at each of the landmarks in the second plurality of landmarks, wherein the second plurality of landmarks is a subset of the first plurality of landmarks; and electronically determining the positions of a third plurality of landmarks based on the positions of the second plurality of landmarks and a predetermined template of standard landmarks, wherein the third plurality of landmarks is a subset of the first plurality of landmarks.

33. A method as defined in claim 30, wherein the step of identifying the first plurality of landmarks located in the first digital image of the face of the person comprises electronically detecting the position of at least one of the landmarks in the first plurality of landmarks.

34. A method as defined in claim 30, further comprising:

electronically creating a second digital image based on the first digital image of the face of the person and the location of the defect areas, the second digital image visually identifying the plurality of defect areas located in the first digital image of the face of the person by electronically altering the color of a plurality of pixels substantially in the area containing the skin defect to at least one color visually distinct from the skin color of the first digital image; and displaying the second digital image on a display.

35. A method as defined in claim 30, further comprising:

determining a first numerical severity associated with the plurality of defect areas located in the first digital image of the face of the person; and generating a comparison between the first numerical severity and a predetermined value associated with a population of people.

36. An apparatus adapted to perform the method of claim 30.

37. A tangible medium storing program instructions adapted to perform the method of claim 30.

38. A method for characterizing skin associated with a face of a person, comprising:

acquiring a first digital image of the face of the person;

electronically determining a sub-image of the first digital image of the face of the person;

electronically analyzing the sub-image of the first digital image of the face of the person to determine an overall skin characteristic associated with the digital image of the face of the person; and determining a comparison between the overall skin characteristic and a predetermined value associated with a population of people.

39. A method as defined in claim 38 further comprising the step of:

generating a second digital image based on the comparison between the overall skin characteristic and the predetermined value; and displaying the second digital image on a display.

40. An apparatus adapted to perform the method of claim 38.

41. A tangible medium storing program instructions adapted to perform the method of claim 38.

* * * * *